United States Patent
Couenne et al.

(10) Patent No.: US 7,192,526 B2
(45) Date of Patent: Mar. 20, 2007

(54) METHOD OF OPTIMIZING THE OPERATION OF A XYLENE SEPARATION UNIT USING SIMULATED COUNTERCURRENT

(75) Inventors: Nicolas Couenne, Lyons (FR); Luc Wolff, Lyons (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 195 days.

(21) Appl. No.: 10/525,960

(22) PCT Filed: Jul. 23, 2003

(86) PCT No.: PCT/FR03/02327

§ 371 (c)(1),
(2), (4) Date: Feb. 28, 2005

(87) PCT Pub. No.: WO2004/020068

PCT Pub. Date: Mar. 11, 2004

(65) Prior Publication Data

US 2006/0006113 A1    Jan. 12, 2006

(30) Foreign Application Priority Data

Aug. 28, 2002    (FR)    ................... 02 10658

(51) Int. Cl.
*B01D 15/08*    (2006.01)

(52) U.S. Cl. ................... 210/659; 210/662; 210/198.2; 585/821; 585/828

(58) Field of Classification Search ............... 210/656, 210/659, 662, 672, 198.2, 264; 585/821, 585/828
See application file for complete search history.

(56) References Cited

U.S. PATENT DOCUMENTS

| | | | | |
|---|---|---|---|---|
| 4,284,580 | A | * | 8/1981 | Logan et al. ............... 554/193 |
| 5,470,482 | A | | 11/1995 | Holt |
| 5,902,486 | A | * | 5/1999 | Couenne et al. ............ 210/659 |
| 5,948,950 | A | * | 9/1999 | Hotier et al. ............... 585/828 |
| 6,045,703 | A | * | 4/2000 | Miller ......................... 210/659 |
| 6,471,870 | B1 | * | 10/2002 | Nicoud et al. .............. 210/659 |
| 6,652,754 | B1 | * | 11/2003 | Pavone ....................... 210/659 |
| 6,896,812 | B1 | * | 5/2005 | Frey ........................... 210/659 |

FOREIGN PATENT DOCUMENTS

| | | |
|---|---|---|
| EP | 0 875 268 A1 | 11/1998 |
| EP | 1 101 516 A1 | 5/2001 |
| WO | WO 01/87452 A2 | 11/2001 |

* cited by examiner

*Primary Examiner*—Ernest G. Therkorn
(74) *Attorney, Agent, or Firm*—Antonelli, Terry, Stout and Kraus, LLP.

(57) ABSTRACT

Method of optimizing the operation of a unit intended for separation of the components of a feed (xylenes) by simulated countercurrent in hybrid operating mode.

The method allows to minimize the solvent ratio and to maximize the capacity of the separation unit while keeping product specifications such as purity and yield constant. It has been verified that these two objectives cannot be reached simultaneously and it is recommended to operate with a minimum solvent ratio while guaranteeing a high capacity compatible with stable operation of the separation unit. These optimization objectives are reached while keeping good stability around the optimum point thus defined, by using a known operation control process such as the one described in patent EP-875,268 for example.

4 Claims, 2 Drawing Sheets

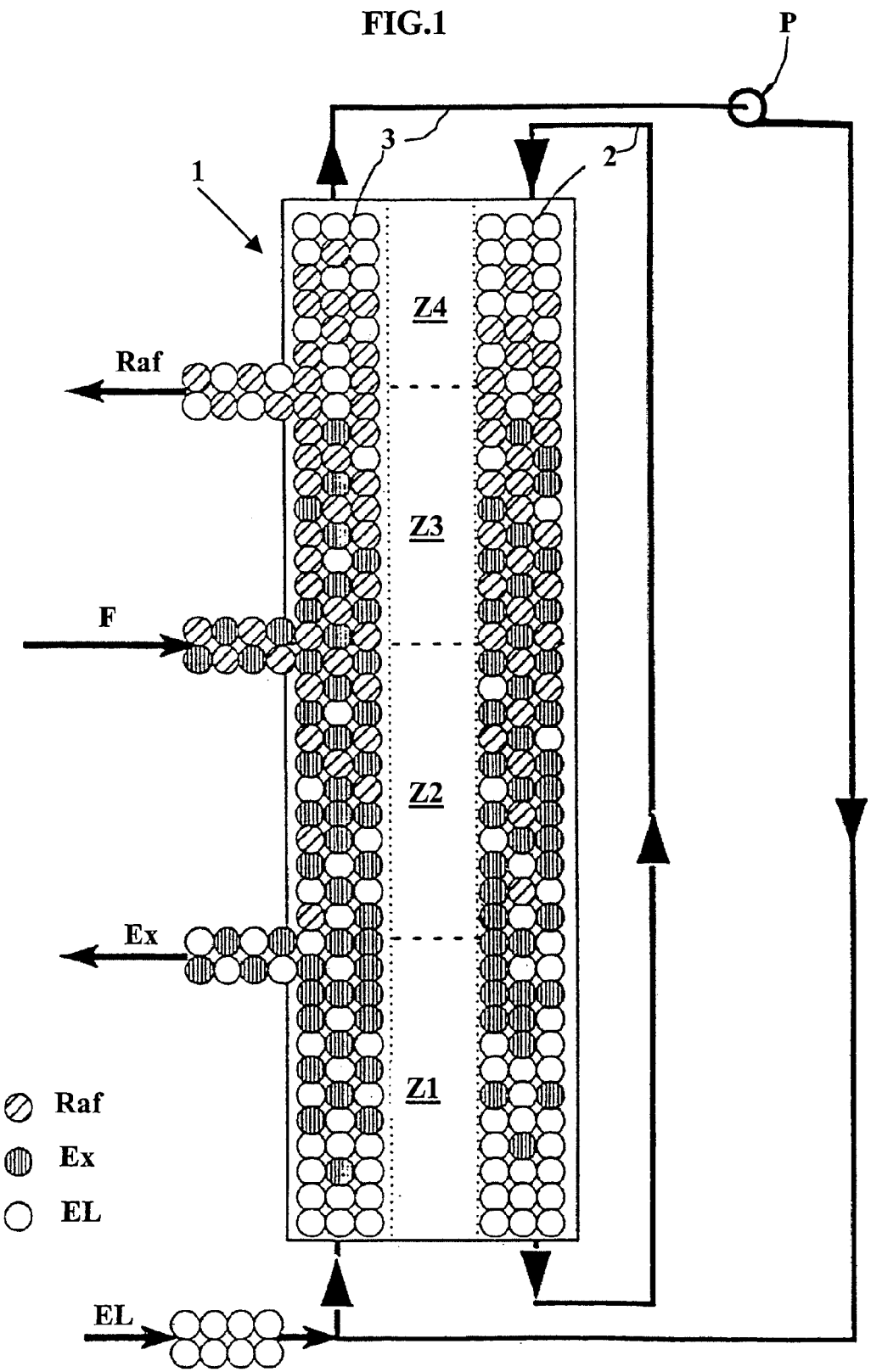

METHOD OF OPTIMIZING THE OPERATION OF A XYLENE SEPARATION UNIT USING SIMULATED COUNTERCURRENT

REFERENCE TO RELATED APPLICATIONS

This application is a 371 of PCT/FR03/02327 filed Jul. 23, 2003.

FIELD OF THE INVENTION

The present invention relates to a method of optimizing operation of a simulated countercurrent xylenes separation method under hybrid operating conditions.

BACKGROUND OF THE INVENTION

Chromatography-based separation or fractionation methods are most often implemented in a separation system comprising (FIG. 1) a series of columns or column fractions interconnected in series, forming a closed loop. A porous solid of predetermined grain size constitutes the stationary phase. The mixture to be separated is fed into the column, then displaced by means of a carrier fluid or desorbent (EL) and the various constituents flow out successively according to whether they are retained more or less greatly by the stationary phase. Injection points for the mixture or feed F containing all of the constituents to be separated and the solvent or desorbent EL, and extraction points for an extract Ex containing the product to be upgraded, diluted in solvent, and for a raffinate Rf containing all the other constituents are distributed along this loop. These points delimit various zones (Z1 to Z4 for example). An identical liquid stream flows through all the columns or column fractions of a zone. A pump P is arranged somewhere in the loop to provide circulation of the fluid in the direction shown in the diagram.

In a real countercurrent separation system, a fixed and constant concentration profile develops where the positions of the injection and extraction points remain fixed. Adsorbent solid 3 and liquid 2 move in a countercurrent flow. A solid entrainment system and recycle pump P, both arranged at the junction of zones Z1 and Z4, respectively allow to send back the solid from the base to the top and, conversely, the liquid from the top to the base.

Systems known as simulated moving bed systems allow to overcome a major difficulty inherent in true moving bed methods, which consists in properly circulating the solid phase without creating attrition and without considerably increasing the bed porosity in relation to the porosity of a fixed bed. To simulate its displacement, the solid is placed in a certain number n of fixed beds (generally $4 \leq n \leq 24$) arranged in series and it is the concentration profile that is displaced at a substantially uniform velocity all around a closed loop. In practice, successive switching of the injection and extraction points is obtained by means of a rotary valve or more simply of a series of suitably controlled on-off valves. This circular switching, carried out at each period, of the different incoming-outgoing liquid flows in a given direction amounts to simulating displacement of the solid adsorbent in the opposite direction.

The separation systems used for xylenes separation most often consist of four main zones. There are also systems with five zones where part of the extract separated from the solvent is reinjected between extract draw-off and feed injection. Others can also have five to seven zones where secondary fluids allow to rinse lines carrying successively several fluids so as to prevent contaminations.

In the text hereunder, the following variables are defined as:

controlled variables: variables that have to be constantly close to a previously determined set value and which show the smooth running of the process. It can be, for example, the purity of the constituents of an extract, the yield of the separation unit for a given constituent, etc.

operating variables: variables that can be modified by the operator, such as the flow rates or the valve switch period allowing to simulate displacement of the beds, etc.

control variables: variables that act mainly on a single zone, for example on the part of the concentration profile contained in a zone. These control variables are determined by the control algorithm and are translated into operating variables.

It can be reminded that the goal of an advanced control system applied to a process is to calculate a control law (all of the values of the operating variables in time) so as to:

control operation, i.e. calculate a control law that can ensure the transition between two distinct values of one or more a priori selected controlled variables, and regulate operation, i.e. calculate a control law allowing best compensation (in advance or at least asymptotically) of all the outside disturbances acting on the process so that the a priori selected controlled variables keep a quasi-constant value.

In the case of a simulated countercurrent separation unit, regulation can also compensate for disturbances due to an evolution with time of the thermodynamic and geometric parameters of the adsorbent (of course for a limited deterioration of the adsorbent properties).

These objectives are reached with the automatic control process based on either a "black box" type technique, or on a more controlled approach allowed by non-linear modelling of the separation process.

Patent EP-875,268 (U.S. Pat. No. 5,902,486) filed by the applicant describes a method intended for automatic control of a simulated moving bed separation system for constituents of a mixture of circulating fluids, notably aromatic hydrocarbons, which can have notable flow rate or feed quality variations. Control of the process (of non-linear multivariable type carried out from a knowledge or linear model in the neighbourhood of a given working point, performed from input/output representation models) is carried out with a certain number of variable measurements at a plurality of measuring points along the loop (concentrations and flow rates for example) and of characteristic measurements of the fluids injected and extracted. Ratios respectively indicative of the ratio, in each zone, between the fluid flow rates and the simulated adsorbent substance flow rates are determined from current controlled variable values (constituents purity, yield of the system, etc.) depending on the measured variables. Values to be given to the operating variables to bring or bring back the controlled variables to determined set values are determined from these ratios. If four independent control variables are available for example, the four ratios in each zone, four controlled variables have to be determined.

The control process comprises a calculating algorithm which determines the ratios from the measurements obtained, which are necessary for calculation of the controlled variables. This calculation can be carried out in two completely different ways: either using a non-linear physical model of the true moving bed separation unit, or using a combination of monovariable linear models, each representing the behaviour of an output (a controlled variable) in relation to an input (a control variable), knowing that combination of these linear models is often referred to as "black box" by specialists. Determination of these simple models is performed from a set of experimental measurements obtained on the process working in a state close to its planned stable state.

In its developed xylenes separation version, the process is used to purify the paraxylene present in feeds containing mostly xylenes, but also C9 aromatics and paraffins in limited amounts. It is available in two versions: the standalone version, which allows to reach a purity above 99.80%, and the hybrid version which is dimensioned to reach a purity of the order of 95.00%. The latter version of the process, described for example in patent EP-531,191, is marketed with addition of a crystallization process allowing to reach the desired high purity. Units working in hybrid mode consist of at least 12 columns, whereas there are at least 24 columns for the standalone mode.

Whether a non-linear automatic control process or a black box type process, the goal is to calculate, from measurement of the concentrations of certain constituents necessary for calculation of controlled variables, ratios (Rk) respectively indicative of the ratio, in each zone, between fluid flow rates (Qk) and the simulated flow rate of adsorbent material (Qs) so as to bring or to bring back the controlled variables to determined set values. In a second stage, the values of the ratios thus determined will be converted to operating variables applied to the process by means of conversion formulas.

The control process thus allows the separation unit to be brought to a working point where the following four parameters are brought to specified values:

1. The purity of the paraxylene in the extract defined as follows:

$$\text{Purity} = \frac{Px^{extract}}{Px^{extract} + IMP^{extract}}, \text{ where}$$

$Px^{extract}$ is the paraxylene concentration in the extract, and $\text{Imp}^{extract}$ represents all the impurities in the extract.

Determination of this controlled variable requires online measurement in the extract, on the one hand, of the paraxylene concentration and, on the other hand, of all of the other constituents;

2. The paraxylene yield of the unit defined as follows:

$$\text{Yield} = 1 - \frac{Q_{raffinate} Px^{raffinate}}{Q_{raffinate} Px^{raffinate} + Q_{extract} Px^{extract}}, \text{ where}$$

$Px^{extract}$ and $Px^{raffinate}$ respectively represent the paraxylene concentration in the extract and in the raffinate, and $Q_{raffinate}$ and $Q_{extract}$ respectively represent the raffinate and extract flow rates.

Determination of this controlled variable requires online measurement of the paraxylene concentration in the extract and in the raffinate, and measurement of the extract and raffinate flow rates.

3. The amount of ethylbenzene $Eb_{extract}$ in the extract. Determination of this controlled variable requires the same online measurement as developed for point 1.

4. The amount of paraxylene $Px_{zone1}$ at a point of zone 1.

Determination of this controlled variable requires development of a specific measuring point in zone 1, i.e. between solvent injection and extract draw-off.

If the first two controlled variables clearly correspond to production objectives, the last two are directly linked with the object of the present invention, i.e. optimization of the unit operation.

Control of the separation unit requires concentration measurements at three distinct points of the loop. These measurements are carried out by means of chromatography or Raman spectrometry, as described in patent FR-2,699,917 (U.S. Pat. No. 5,569,808) filed by the applicant. Online calculation of the purity and of the yield and measurement of the amount of ethylbenzene in the extract requires two measurements which provide the concentrations of the different constituents in the extract and in the raffinate. The last output $Px_{zone1}$ requires a measuring point in zone Z1. The length of an analysis ranges between some seconds (Raman spectrometry) and 20 minutes (chromatography). Considering the response time of the unit (between 4 and 8 hours), the quality of the process control is not affected by the analysis time if it remains less than one hour.

Conversion of the control variables (ratios Rk) to "conventional" operating variables is always possible, apart from the real physical application constraints linked with the dimensioning of the process and its equipment, because there is a one to one relation between them, a necessary condition for making the separation system perfectly controllable.

It is well-known that operation of a simulated countercurrent separation system is nearly identical to that of a true moving bed system if, for the latter, the flows circulating countercurrent to the main liquid flow meet the equivalence relations described in the aforementioned patent EP-875,268.

The control variables (ratios Rk) are determined in relation to these equivalences as the dimensionless ratios between the main liquid flow rates in each zone and the solid flow rate which is constant in the whole separation unit:

$$R_k = \frac{Q_k}{Q_s}.$$

Selection of these ratios follows from writing of the material balance equations of the model of a true moving bed separation unit in the stationary state in a column portion that is discretized. The number of ratios is equal to the number of zones that make up the unit, each zone being characterized by a main liquid flow rate distinct from the contiguous zones.

SUMMARY OF THE INVENTION

The method according to the invention allows to optimize operation of a unit intended for separation of the constituents of a feed and comprising a separation loop consisting of the interconnection of a series of beds containing a solid adsorbent material forming several zones delimited by feed and solvent injection points and extraction points for discharge, out of the loop, of an extract containing a first constituent of the feed, and of a raffinate, injection points and extraction points switching means allowing to simulate countercurrent displacement of the beds and means for measuring operating variables.

It comprises using a control algorithm for bringing the separation unit to a working point where the purity of the first constituent in the extract (such as paraxylene for example) and the yield of the separation unit as regards production of this first constituent are brought to specified values.

According to a first implementation mode, for a given value of the concentration, in the extract, of a second constituent of the feed (such as ethylbenzene for example), the set value of the concentration of the first constituent is adjusted in a zone located between the solvent injection point and the extract extraction point so as to minimize the proportion of solvent in relation to the feed.

Adjustment of the set concentration value is advantageously obtained by means of a monovariable optimizer.

Adjustment of the set concentration value of the second constituent in the extract is preferably achieved to maximize the capacity of the separation unit within the working stability limits of said unit.

According to another implementation mode, the set value of the concentration, in the extract, of the second constituent of the feed is adjusted to obtain maximization of the capacity of the separation unit within the working stability limits of said unit.

The set concentration value, in the extract, of the second constituent preferably ranges between 0.02% and 2%.

BRIEF DESCRIPTION OF THE FIGURES

Other features and advantages of the method according to the invention will be clear from reading the description hereafter of an embodiment given by way of non limitative example, with reference to the accompanying drawings wherein:

FIG. 1 diagrammatically shows a separation unit with four zones having intercalated injection and extraction points, FIGS. 2a, 2b respectively show the variation of the solvent ratio (S/F) and of the mean recycle flow rate (MR) as a function of $Px_{zone\ 1}$ and $Eb_{extract}$.

DETAILED DESCRIPTION

Figure 2A:
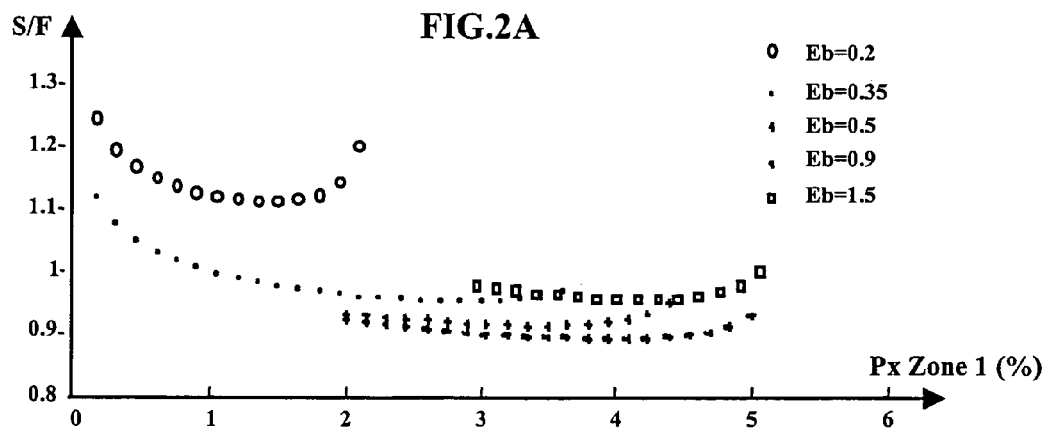

The method according to the invention allows to optimize operation of a xylenes separation unit in hybrid mode with four zones, first brought, by applying the control process which is the object of the aforementioned patent EP-875,268, to a working point where two controlled variables characterizing directly the quality and the production of the product, i.e. the purity of the paraxylene in the extract and the paraxylene yield defined above, are brought to specified values.

Optimization is conducted using the control algorithm described therein. In order to optimize operation, since we have four independent control variables (the four ratios of each zone) and since two other controlled variables have to be determined, we act upon:

the ethylbenzene concentration in the extract, $Eb_{extract}$, that can be advantageously determined using the measuring means used for measuring the purity, and the paraxylene concentration at a given point of zone Z1 (defined as the zone contained between solvent injection and extract draw-off), $Px_{zone1}$, which can be determined by measuring the paraxylene concentration at a given point of zone Z1.

The ethylbenzene concentration in the extract allows to characterize the position of the ethylbenzene profile in zone Z2. The paraxylene concentration at a given point of zone Z1 is determined to control the paraxylene flow downstream from the solvent injection point.

The last two controlled variables are used to maximize or to minimize a functional defined as a function of a priori set production objectives (economic cost for example) for this type of separation unit, such as, for example:

1. Minimization of the solvent ratio defined as the ratio between the solvent flow rate and the feed flow rate.
2. Maximization of the feed flow rate.
3. Minimization of the mean recycle flow rate defined as follows:

$$Q_{mean} = \frac{1}{Nb_{column}} \sum_{i=1}^{NbZone} l_i Q_i, \text{ where}$$

$Nb_{Zone}$ represents the number of zones of the unit
$Nb_{column}$ represents the total number of columns
$l_i$ represents the number of columns in each zone
$Q_i$ represents the liquid flow rate in each zone.

Only points 1 and 2 are going to be dealt with in the description hereafter, because optimization of point 3 is equivalent to that of point 2.

Points 2 and 3 are optimized together because they are connected by the homogeneity of the system of equations relating the ratios and the operating variables. Any flow rate increase can be compensated by an equivalent increase in the other flow rates and a decrease in the same proportion of the valve switching period. Maximization of the feed flow rate can therefore be directly associated with minimization of the recycle flow rate in the sense where the lower the recycle flow rate, the greater the margin for increasing the feed flow rate. These "ideal" considerations are limited in practice by hydrodynamics such as, for example, the increase in the axial dispersion which varies quadratically with the velocity of the fluid in the outside porosity.

Point 1 relates to the excess consumption of solvent whose distillation cost is high. Optimization of the separation unit, in the sense of points 1 and 2, is obtained by judicious adjustment of the outputs $Px_{zone1}$ and $Eb_{extract}$.

Simulation Results

We show with the simulation that these optimization objectives are not independent and that there is an absolute minimum for the solvent ratio depending both on $Px_{zone1}$ and $Eb_{extract}$. We will see, with the experimental results, that we recommend operation under optimum conditions (to guarantee unit stability) however allowing to obtain a significant solvent ratio and capacity gain.

Figure 2B:
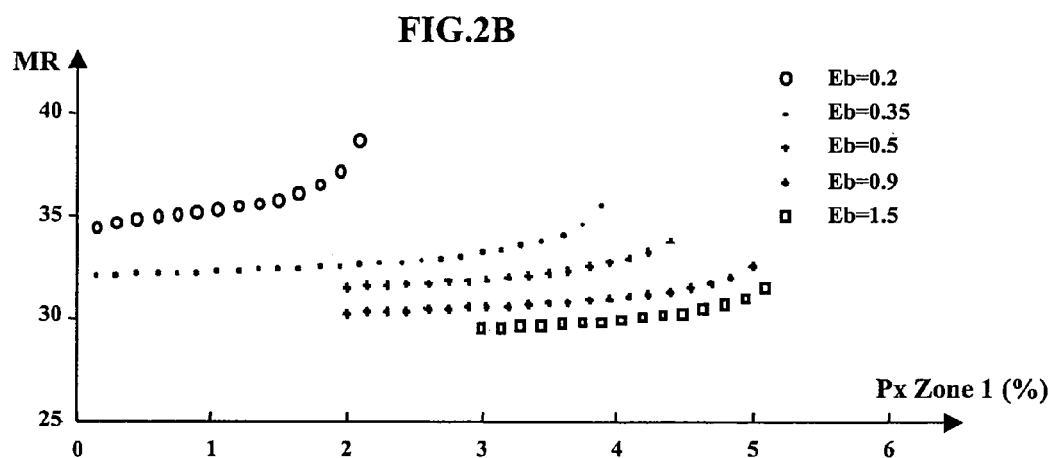

The results obtained with simulation are summarized in the graphs of FIG. 2.

The curves represent the variation of the solvent ratio (S/F) and of the mean recycle flow rate as defined above, as a function of the value of $Px_{zone1}$ (abscissa) for a given $Eb_{extract}$ value, at constant purity, constant yield and constant feed flow rate.

The variations of (S/F) are strictly concave both in relation to $Px_{zone1}$ (obvious from the curves) and to $Eb_{extract}$ since the curve ($Eb_{extract}$=1.5%) is above curves ($Eb_{extract}$=0.5%) and ($Eb_{extract}$=0.9%) and below curve ($Eb_{extract}$=0.35%). There is therefore an absolute minimum for (S/F) whose value is not represented in these curves.

The variation of the mean recycle flow rate (MR) in relation to $Px_{zone1}$ and $Eb_{extract}$ is strictly increasing monotonous. The value of the mean recycle flow rate (MR) decreases when $Eb_{extract}$ increases and increases when the value of $Px_{zone1}$ increases, all the other specifications being constant.

The results presented above show that simultaneous optimization of points 1 and 2 (i.e. minimization of S/F and maximization of the feed flow rate) is not possible. There is an absolute minimum for (S/F) which does not correspond to the possible minimum likely to be reached by the mean recycle flow rate.

Experimental Results

The experimental results obtained in the pilot unit confirm the tendencies shown by the simulation.

In the example hereafter, only the effect of $Px_{zone1}$ is presented because the influence of $Eb_{extract}$ on the unit operation is clearly more evident and therefore requires no specific experiments.

Comparison of the following 2 stationary points:

| Stationary point No. 1 | Stationary point No. 2 |
| --- | --- |
| Purity = 95% | Purity = 95% |
| Yield = 96% | Yield = 96% |
| $Eb_{extract}$ = 0.06% | $Eb_{extract}$ = 0.06% |
| $Px_{zone1}$ = 4% | $Px_{zone1}$ = 1.8% |
| $Q_{feed}$ = 68 cc/min | $Q_{feed}$ = 78 cc/min |
| $Q_{recycle}$ = 379 cc/min | $Q_{recycle}$ = 379 cc/min |
| S/F = 1.15 | S/F = 1.1 | shows that, for the same purity and yield specifications, it is possible to pass 10 cc/min feed more, to obtain a slightly lower solvent ratio and to keep the same recycle flow rate by changing only the set value of $Px_{zone1}$.

Characteristics of the Optimum Points Obtained

In order to compare the different optimum points (in the sense of the minimization of (S/F)) obtained above by simulation, we trace on the following graph all of the concentration profiles C along the columns of the separation loop for three significant values of $Eb_{extract}$.

Figure 3:
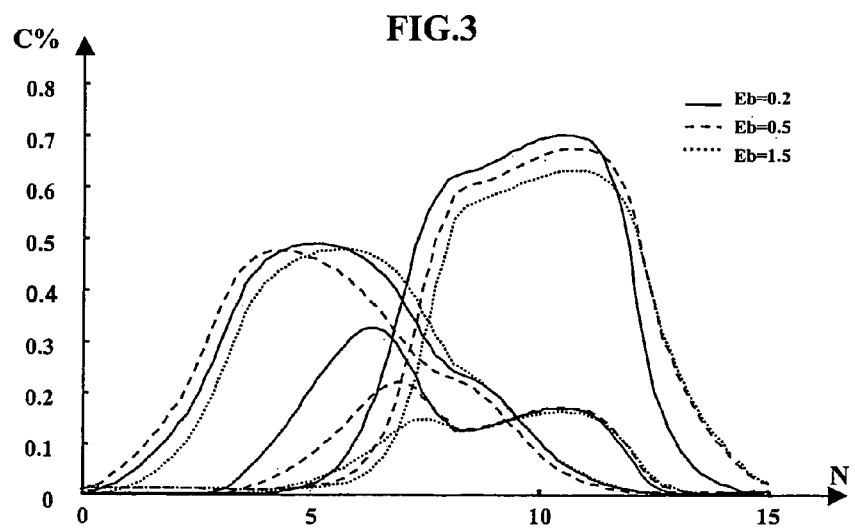
FIG. 3 shows the concentration profiles (C %) of Px, Eb, Mox along the separation loop at the optimum working points in the sense of (S/F), at constant purity and yield.

The vertical lines of the graph of FIG. 3 respectively represent, from left to right: extract draw-off point Vex, feed injection point $V_F$ and raffinate draw-off point $V_{RAF}$.

The profiles go down when the mean recycle profile decreases. Close to extract draw-off point Vex, the various profiles are quite distinct because the proportions between the impurities in the extract vary substantially since one of them (ethylbenzene) is the parameter characterizing these simulations. In zone Z3, contained between feed injection $V_F$ and raffinate draw-off $V_{RAF}$, the profiles of the various simulations are rather "close". Their shape clearly characterizes the optimum operating modes of this separation unit, i.e. raffinate extraction is always at the base of the paraxylene profile in zone Z3. The differences obtained for the paraxylene concentration value at the level of the raffinate draw-off can be explained by a constant yield value for all the simulations. The small variations of the Px concentration value compensate for the variations of the raffinate flow rate value specific to each simulation.

Separation Unit Optimization and Operation

After examining the results obtained by simulation, completed by the experimental results, we can set out the following rules for optimum operation of the separation unit in hybrid mode in the sense of minimization of ratio (S/F) and of maximization of the capacity, i.e. adjustment of the separation unit so that it can potentially process a maximum amount of feed. Application of this optimization strategy is possible in practice only by means of a control algorithm such as, for example, the algorithm presented in the aforementioned patent EP-531,191.

Judicious selection of set values $Px_{zone1}$ and $Eb_{extract}$ allows to reach the separation unit operation optimum in the sense of minimization of (S/F) for a given purity and yield.

Considering that we know, from the surveys carried out by simulation, that the curves are always strictly concave (FIG. 2) and that, by varying $Px_{zone1}$, we can move along such curves, and because of the constraints imposed on set value $Eb_{extract}$ to guarantee maximization of the capacity while guaranteeing unit stability, a very simple simplex type monovariable optimizer, well-known to specialists, can be used for iterative automatic online search for the optimum set value of $Px_{zone1}$. Such an optimizer is practical because it can work without having to calculate numerical gradients. The advantage is that it limits the number of evaluations of the cost function which, in the case of the present method, correspond to as many working points of the separation unit potentially outside the optimum working point.

Within the context of this application, optimization will be achieved with generation of triangles in the plane, each vertex of the triangle being a potential solution. At each stage of the search for the optimum, a new point, in the current triangle, or close thereto, will be produced. The value of the function at the new point is compared with the values of the function at the vertices of the simplex, and usually one of the vertices is replaced by the new point, thus giving a new simplex and a better estimation of the cost function. This stage is repeated until the diameter of the simplex is smaller than the tolerance selected.

Judicious selection of set value $Eb_{extract}$ allows to guarantee maximization of the unit capacity, but with the following two comments:

1. The optimum value of this set value cannot be reached because, in this case, the operating conditions reached by the unit are not stable. In fact, a very slight decrease in the recycle flow rate generates an increasing amount of ethylbenzene accumulated in the column, which makes the separation unit difficult to operate because the dynamics of increase of the amount of ethylbenzene in the extract is much faster than the decrease dynamics.

2. The optimum set value for $Eb_{extract}$ in terms of capacity does not coincide with the value sought for optimizing (S/F), which is smaller.

Considering the two comments above, it is preferable to favour the separation unit stability and to select, in this context, a set value $Eb_{extract}$ guaranteeing maximization of the capacity, without trying to reach the possible optimum. In this configuration, optimization of (S/F) amounts to the optimization described above.

Considering the experimental and simulation results, the value selected for $Eb_{extract}$ directly depends on the performance of the control system of the separation unit and on the purity value selected.

The steepness of the profile (all the profiles of the various simulations are similar) in zone Z3 and the specific position of the extraction point for raffinate Raf at the base of this front show a high sensitivity of the yield value to small flow rate variations or to any other disturbances generating a variation in the position of the profile. This high yield sensitivity shows that operation of a unit at its optimum point is difficult manually.

The invention claimed is:

1. A method of optimizing operation of a unit intended for separation of the constituents of a feed, comprising a separation loop consisting of the interconnection of a series of beds containing a solid adsorbent material forming several zones delimited by feed (F) and solvent (S) injection points and extraction points for discharge, out of the loop, of an extract (Ex) containing a first constituent (Px) of the feed, and of a raffinate (Raf), injection points and extraction points switching means allowing to simulate countercurrent displacement of the beds and means for measuring operating variables, comprising using a control algorithm for bringing the separation unit to a working point where the purity of the first constituent in the extract and the yield of the separation unit as regards production of this first constituent are brought to specified values, characterized in that, for a given value of concentration ($Eb_{extract}$), in the extract, of a second constituent (Eb) of the feed, the set value of the concentration ($Px_{zone1}$) of the first constituent is adjusted manually in a zone (Z1) located between the solvent injection point and the extract extraction point so as to minimize the solvent/feed ratio (S/F).

2. A method as claimed in claim 1, characterized in that said concentration value ($Eb_{extract}$) is adjusted so as to maximize the capacity of the separation unit within the operating stability limits of said unit.

3. A method as claimed in claim 1, characterized in that said set value of concentration ($Px_{zone1}$) is adjusted by means of a monovariable optimizer.

4. A method as claimed in claim 1, characterized in that the first constituent and the second constituent of the feed are paraxylene and ethylbenzene respectively.

* * * * *